United States Patent
Wells

(10) Patent No.: US 11,013,879 B2
(45) Date of Patent: May 25, 2021

(54) NON-LOOPING NASAL CANNULA

(71) Applicant: Noel E. Wells, Cape Canaveral, FL (US)

(72) Inventor: Noel E. Wells, Cape Canaveral, FL (US)

(*) Notice: Subject to any disclaimer, the term of this patent is extended or adjusted under 35 U.S.C. 154(b) by 0 days.

(21) Appl. No.: 16/113,298

(22) Filed: Aug. 27, 2018

(65) Prior Publication Data
US 2018/0361098 A1 Dec. 20, 2018

Related U.S. Application Data

(63) Continuation-in-part of application No. 16/008,718, filed on Jun. 14, 2018, now Pat. No. 10,434,274.

(60) Provisional application No. 62/520,222, filed on Jun. 15, 2017.

(51) Int. Cl.
*A61M 16/06* (2006.01)
*A61M 16/08* (2006.01)

(52) U.S. Cl.
CPC .... *A61M 16/0666* (2013.01); *A61M 16/0672* (2014.02); *A61M 16/0683* (2013.01); *A61M 16/0605* (2014.02); *A61M 16/0875* (2013.01); *A61M 2202/0208* (2013.01); *A61M 2210/0618* (2013.01)

(58) Field of Classification Search
CPC .......... A61M 16/0666; A61M 16/0683; A61M 16/0605; A61M 16/0875; A61M 2210/0618; A61M 2202/0208
See application file for complete search history.

(56) References Cited

U.S. PATENT DOCUMENTS

| | | | | |
|---|---|---|---|---|
| 5,335,659 A | * | 8/1994 | Pologe | A61B 5/02427 128/207.18 |
| 6,669,712 B1 | * | 12/2003 | Cardoso | A61M 16/0666 128/200.24 |
| 2004/0045553 A1 | * | 3/2004 | Cardoso | A61M 16/0666 128/207.18 |
| 2011/0146685 A1 | * | 6/2011 | Allan | A61M 16/0616 128/205.25 |
| 2012/0167894 A1 | * | 7/2012 | O'Leary | A61M 16/0666 128/207.18 |
| 2013/0306078 A1 | * | 11/2013 | Lanciotto | A61M 16/0666 128/207.18 |
| 2015/0090255 A1 | * | 4/2015 | Gulliver | A61M 25/02 128/202.15 |
| 2016/0367773 A1 | * | 12/2016 | Davi | A61M 16/0666 |

* cited by examiner

*Primary Examiner* — Timothy A Stanis
(74) *Attorney, Agent, or Firm* — Allen Dyer Doppelt & Gilchrist, PA

(57) ABSTRACT

A non-looping nasal cannula device includes dual nasal prongs extending from a connection bracket and adapted to slide into both nostrils of a user to supply oxygen. The nasal cannula device further includes an oxygen delivery port extending from the connection bracket and configured to be attached to an oxygen tube. An attachment device is secured to the connection bracket and configured to be attached to a user's nose and/or skin in close proximity to the user's nose without looping around the user's ears.

14 Claims, 16 Drawing Sheets ial Patent Application Ser. No. 62/520,222, filed on Jun. 15, 2017, the
NON-LOOPING NASAL CANNULA

CROSS-REFERENCE TO RELATED APPLICATION

This application is a continuation-in-part of U.S. patent application Ser. No. 16/008,718, filed on Jun. 14, 2018, which claims the benefit of U.S. Provisional Patent Application Ser. No. 62/520,222, filed on Jun. 15, 2017, the contents of which applications are herein incorporated by reference in their entirety.

FIELD OF THE INVENTION

The present invention generally relates to a nasal cannula device, and more particularly, to a non-looping nasal cannula device that can be securely attached to a patient.

BACKGROUND OF THE INVENTION

A nasal cannula is a device used to deliver oxygen or airflow to a patient for respiration. A portable oxygen generator or a wall connection in a hospital connected to an immobile oxygen generator is used to supply oxygen to the patient using the nasal cannula. The nasal cannula generally consists of a lightweight plastic tube with two nasal prongs that fit inside the nostrils of the patient. The nasal cannula is conventionally looped behind the patient's ears. Respiratory oxygen can flow directly to the patient's respiratory system when the nasal cannula is secured in place.

A nasal cannula is often secured by taping it to the patient's cheekbones and looping the tube around the patient's ears or by using an elastic headband. The traditional "loop" cannula is, however, non-ideal. It rubs and chafes the sulcus area of skin behind a patient's ears and nostrils, causing significant patient discomfort and increased potential for intentional or unintentional removal of the apparatus by the patient.

Moreover, the nasal cannula is susceptible to accidental dislodging from the nostrils, for example, in patient movement and especially during sleep, unconscious movement or involuntary movement. Caregivers have constantly to check on a patient's cannula device and reposition it. A lack of oxygen can exasperate health conditions and can be life threatening. Dislodging of nasal cannula can increase health care costs and subject a patient to even more distress.

There has therefore been a long-standing need to improve methods of securing a nasal cannula. Despite significant recent advancements in this area, further improvements are possible.

SUMMARY OF THE INVENTION

In view of the foregoing, it is an object of the present invention to provide a non-looping nasal cannula device having improved stabilization and comfortability. According to one embodiment of the present invention, a non-looping nasal cannula device includes dual nasal prongs extending from a connection bracket and adapted to slide into both nostrils of a user to supply oxygen. The nasal cannula device further includes an oxygen delivery port extending from the connection bracket and configured to be attached to an oxygen tube. An attachment device is secured to the connection bracket and configured to be attached to a user's nose and/or skin in close proximity to the user's nose.

According to another embodiment of the present invention, a method of using the nasal cannula device includes connecting an oxygen tube to the oxygen delivery port of the nasal cannula device and securing the attachment device of the nasal cannula device to a user's nose or skin in close proximity of the user's nose without looping around the user's ears.

These and other objects, aspects and advantages of the present invention will be better appreciated in view of the drawings and following detailed description of preferred embodiments.

BRIEF DESCRIPTION OF THE DRAWINGS

Features and benefits of the present invention will become apparent as the description proceeds when taken in conjunction with the accompanying drawings in which.

DETAILED DESCRIPTION OF PREFERRED EMBODIMENTS

Figure 1A:
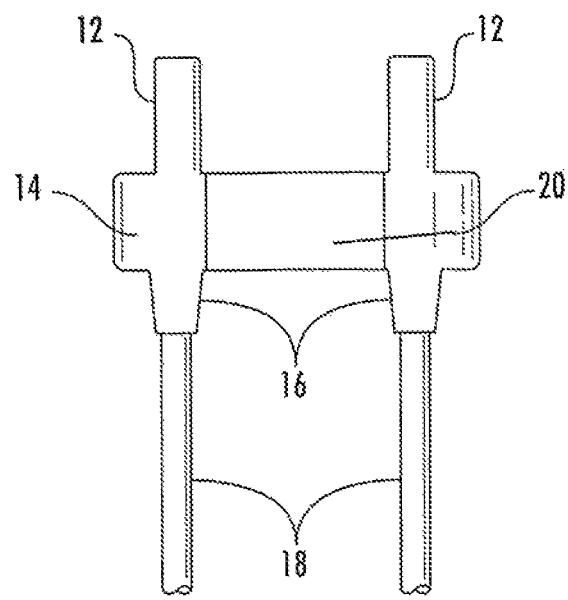
FIG. 1A is a front view of a non-looping nasal cannula device according to one embodiment of the present invention.
Figure 1B:
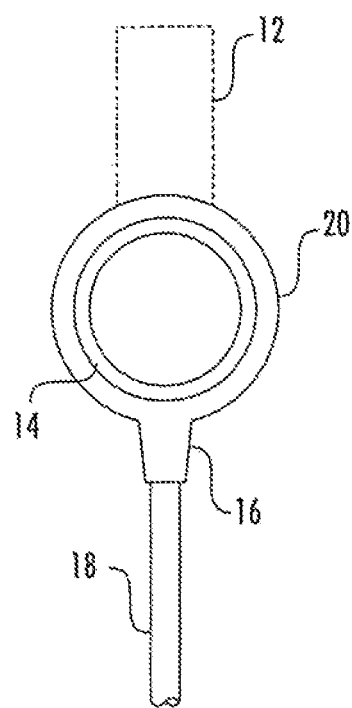
FIG. 1B is a side view of the non-looping nasal cannula device of FIG. 1A.
Figure 2A:
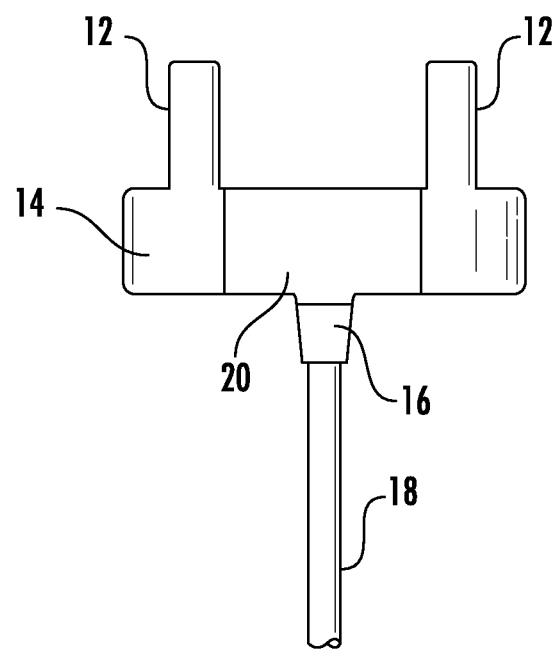
FIG. 2A is a front view of a non-looping nasal cannula device according to another embodiment of the present invention.
Figure 2B:
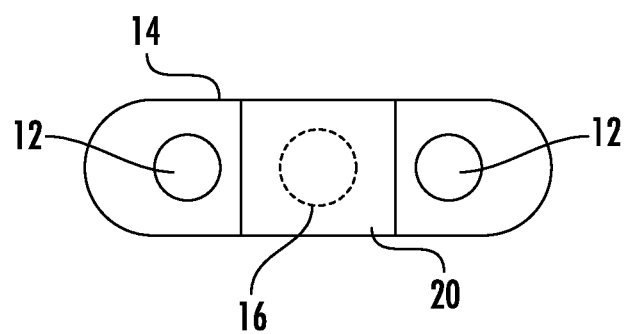
FIG. 2B is a top view of the non-looping nasal cannula device of FIG. 2A.
Figure 2C:
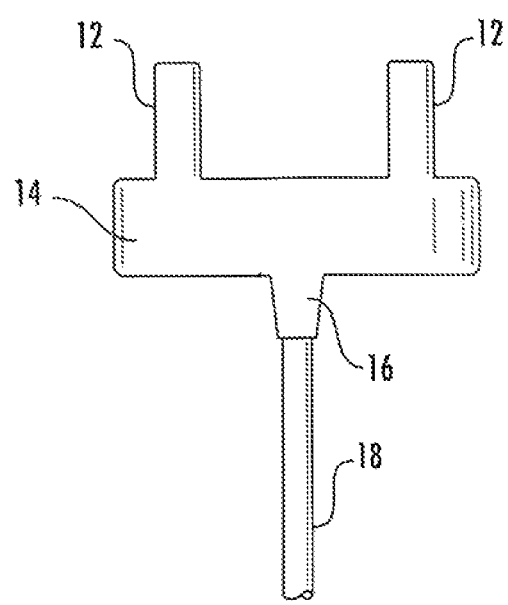
FIG. 2C is a front view of the non-looping nasal cannula device of FIG. 2A without enclosure covering connection bracket of the nasal cannula device.
Figure 3A:
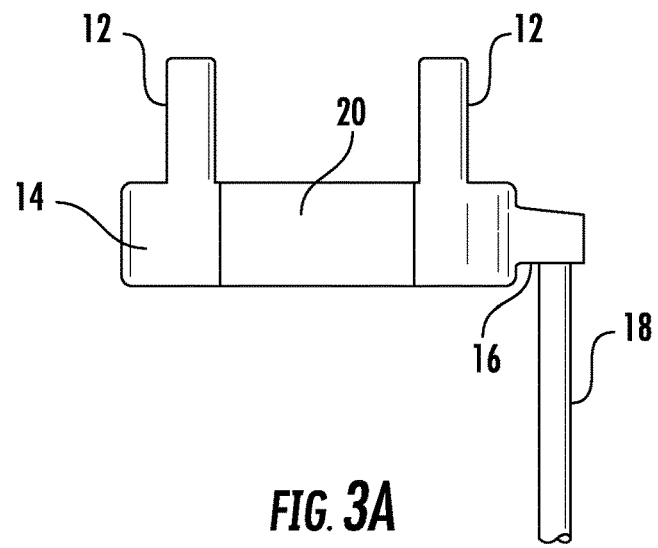
FIG. 3A is a front view of a non-looping nasal cannula device, according to another embodiment of the present invention.
Figure 3B:
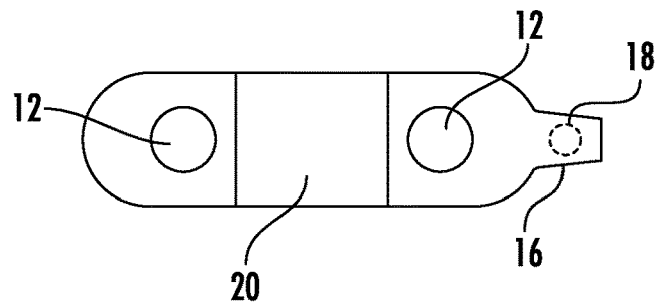
FIG. 3B is a top view of the non-looping nasal cannula device of FIG. 3A.
Figure 3C:
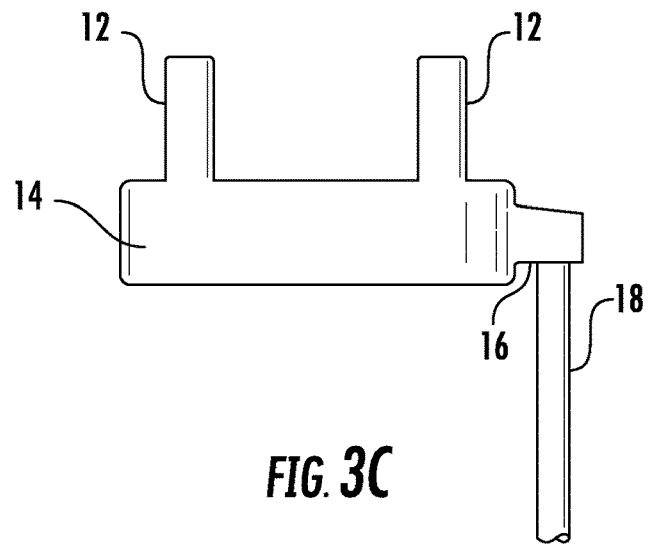
FIG. 3C is a front view of the non-looping nasal cannula device of FIG. 3A without enclosure covering connection bracket of the nasal cannula device.
Figure 4:
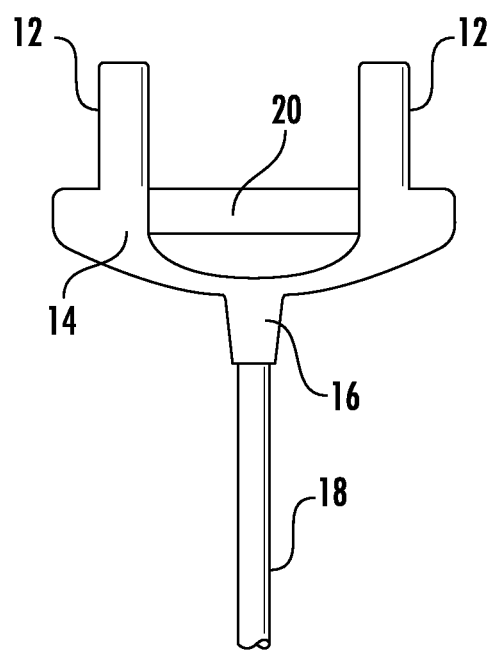
FIG. 4 is a front view of a non-looping nasal cannula device, according to another embodiment of the present invention.
Figure 5A:
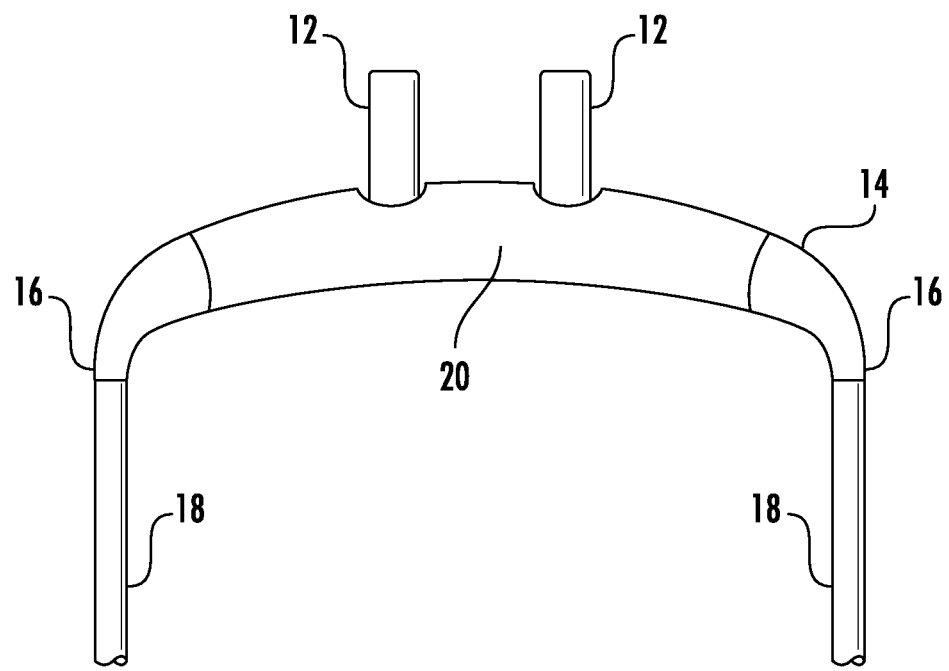
FIG. 5A is a front view of a non-looping nasal cannula device, according to another embodiment of the present invention.
Figure 5B:
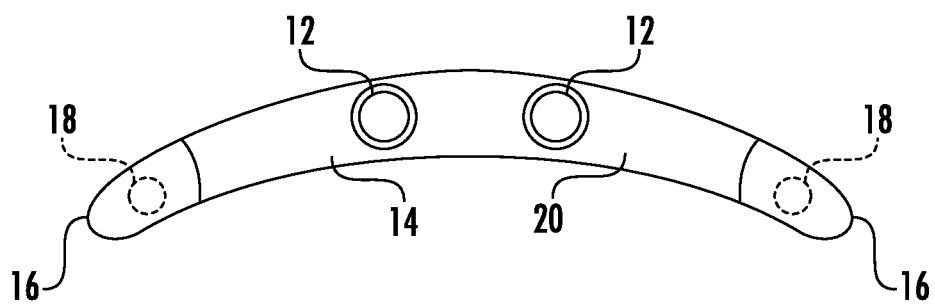
FIG. 5B is a top view of the non-looping nasal cannula device of FIG. 5A.
Figure 6A:
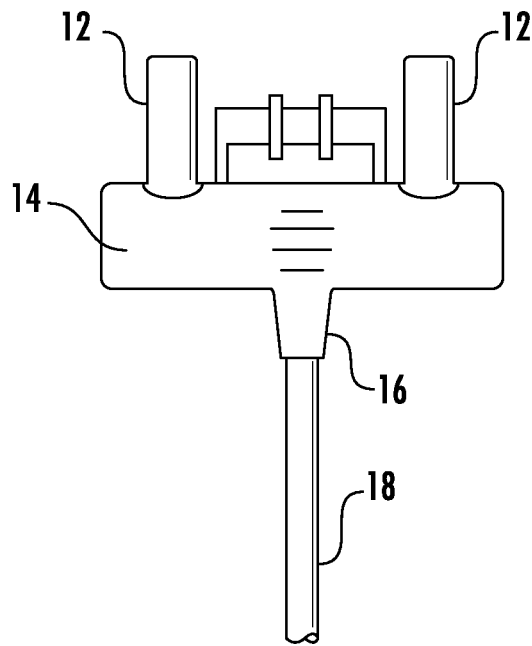
FIG. 6A is a front view of the non-looping nasal cannula device, according to another embodiment of the present invention.
Figure 6B:
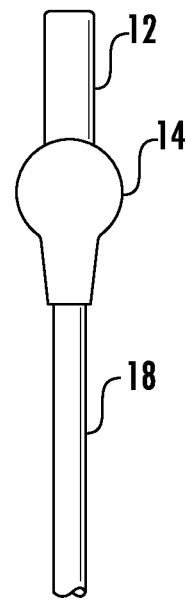
FIG. 6B is a side view of the non-looping nasal cannula device of FIG. 6A.
Figure 6C:
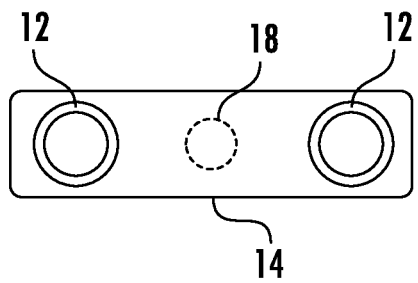
FIG. 6C is a top view of the non-looping nasal cannula device of FIG. 6A.

The present invention will now be described more fully hereinafter with reference to the accompanying drawings, in which various embodiments of the invention are shown. This invention may, however, be embodied in many different forms and should not be construed as limited to the embodiments set forth herein. Rather, these embodiments are provided so that this disclosure will be thorough and complete, and fully convey the scope of the invention to those skilled in the art. Like numbers refer to like elements throughout.

According to one embodiment of the present invention, referring to FIGS. 1A-7B, a nasal cannula device 10 includes dual nasal cannula prongs 12 extending from a connection bracket 14 and an oxygen delivery port 16 extending from the connection bracket 14. Respiratory oxygen is transferred from the oxygen delivery port 16 to the dual nasal cannula prongs 12 via a lumen inside the connection bracket 14. The connection bracket 14 can be of any shape adapted for the connection purpose.

The dual nasal cannula prongs 12 are adapted to slide into the nostril of a user and the oxygen delivery port 16 is configured to be attached to an oxygen delivery tube 18 and thereby connected to an oxygen source.

The nasal cannula devices can further includes an optional enclosure 20 for covering over the connection bracket 14 and providing a rigid or semi-rigid support structure molded over the connection bracket 14 with respective openings for the dual nasal prongs 12 and the at least one oxygen deliver port 16. The enclosure 20 can provide stability and reinforcement for the interconnections between the two nasal prongs 12 and the at least one oxygen deliver port 16. The enclosures 20 are preferably made of a light-weight material such as plastic and other suitable polymer materials. Additionally, the enclosure 20 can include one or more vertical grooves to facilitate centering the device to the columella. The one or more grooves can extend completely around the enclosure 20 or extend only at the bottom of the enclosure 20. The one or more grooves can be used as center indicator and prevent the cannula device from shifting out of place and keep the cannula perfectly centered.

Referring to FIGS. 7A-16, an attachment device 26 is connected to the connection bracket 14 and configured to be attached to a user's nose or skin in close proximity to the user's nose. The attachment device 26 is connected to a respective enclosure 20 and configured to be attached to a user's nose or skin in close proximity to the user's nose.

Figure 7A:
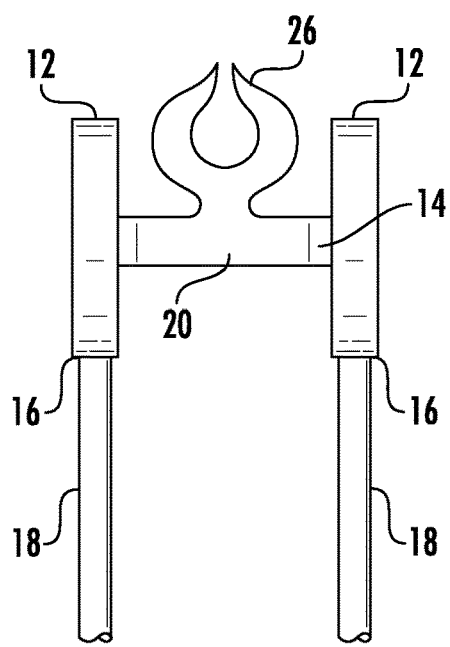
FIG. 7A is a front view of the non-looping nasal cannula device having an attachment device, according to another embodiment of the present invention.
Figure 7B:
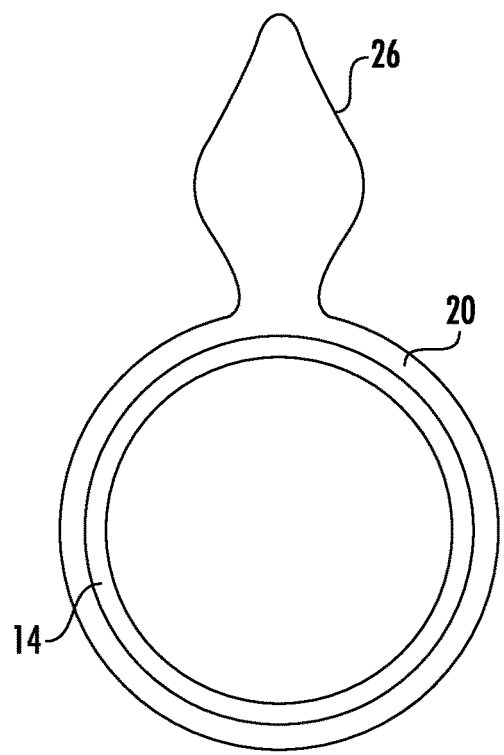
FIG. 7B is cross sectional view of the non-looping nasal cannula device of FIG. 7A.

Referring to FIGS. 7A and 7B, according to one embodiment of the present invention, the attachment device includes a pair of opposing legs having a predefined opening therebetween, and the pair of opposing legs are configured to slide over a nasal septum and biased to be together to provide compression as the pair of legs are moved apart when sliding over the nasal septum. The opposing legs 26 are biased to provide compression as the legs 26 are slightly moved apart when sliding over the nasal septum (not shown). A width between the legs 26 may vary with the patient, but this width must be smaller than the width of the nasal septum. For example, a small width between the legs 26 is required for a proper fit over the nasal septum of a child, and a larger width is required for an adult. The legs 26 may be U-shaped with rounded edges and corners to minimize any discomfort to the patient. In addition, gel pads or other cushioning material may be secured to an inside portion of the legs 26 to soften the contact area of the cannula device 10 to the nasal septum.

Figure 8:
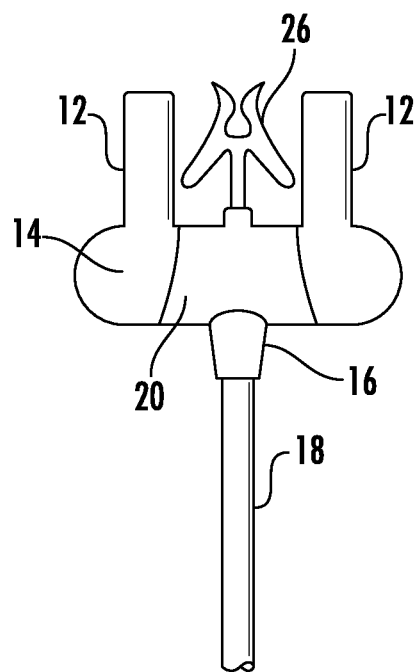
FIG. 8 is a front view of a non-looping nasal cannula device having an attachment device, according to another embodiment of the present invention.

Referring to FIG. 8, according to another embodiment of the present invention, the attachment device 26 includes a prong, and a pair of opposing legs are at a distal portion of a prong, and the pair of opposing legs are configured to be between a closed state and an open state by manipulation of a proximate end of the prong. The prong can be manipulated by pinching its proximate ends. As the proximate ends of the prongs are pressed together and pressure is applied, the opposing distal ends of the prongs move further apart about a fulcrum location. This manipulation allows the prongs to slide over the nasal septum without requiring tissue of the nasal septum to spread the prongs. Accordingly, once the cannula device is in the desired location, the pressure on the proximate ends of the prongs can be released, causing the distal ends of the prongs to move closer together and remain securely attached to the nasal septum, as the width between the prongs is less than the width of the nasal septum.

Figure 9:
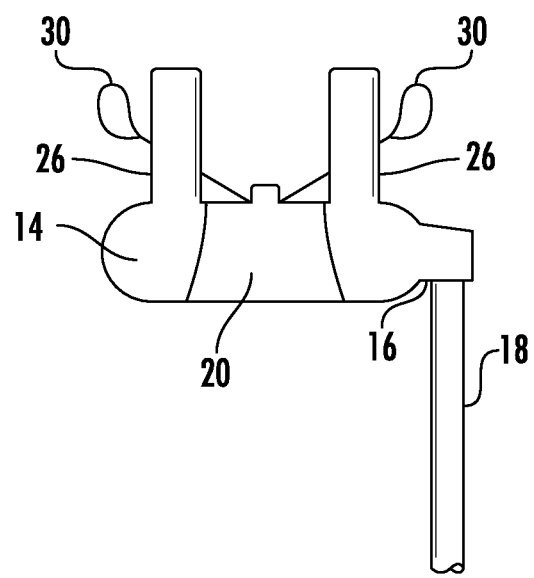
FIG. 9 is a front view of a non-looping nasal cannula device having an attachment device, according to another embodiment of the present invention.
Figure 10:
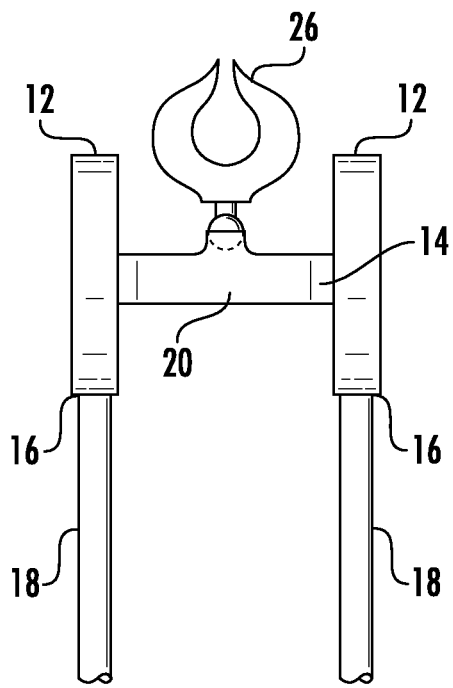
FIG. 10 is a front view of a non-looping nasal cannula device having an attachment device, according to another embodiment of the present invention.
Figure 11:
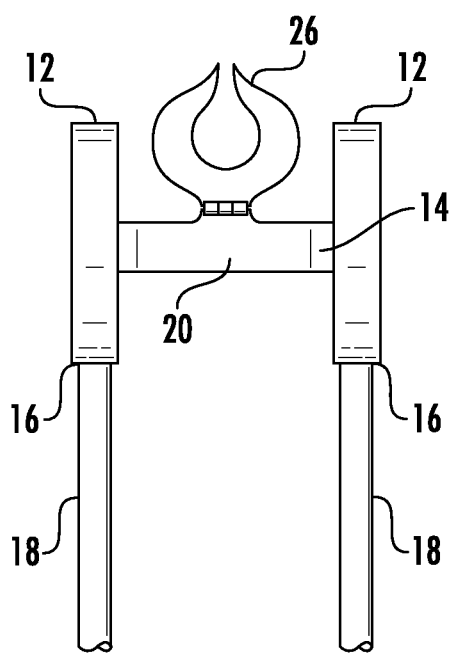
FIG. 11 is a front view of a non-looping nasal cannula device having an attachment device, according to another embodiment of the present invention.

Referring to FIG. 9, according to another embodiment of the present invention, a pair of opposing legs 26 are flexible and the distance between the opposing legs 26 can be adjustable. A pair of gel pads 30 are attached at the ends of the opposing legs 26 and configured for being inserted into and attached to the inner surface of the nostril. This will improve patient comfort, and the pair of gel pads 30 can push the nostril inner surface outward, making the nostril cavity a little wider and facilitating easier breathing.

Figure 12A:
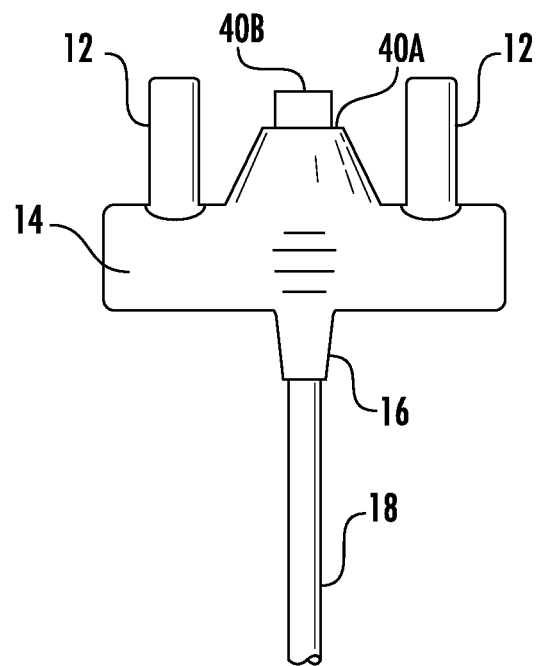
FIG. 12A is a front view of a non-looping nasal cannula device having an attachment device, according to another embodiment of the present invention.
Figure 12B:
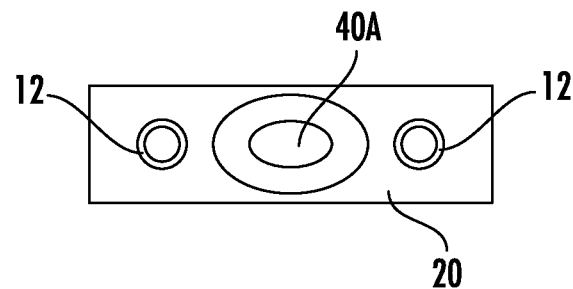
FIG. 12B is a top view of the non-looping nasal cannula device of FIG. 12A.
Figure 13A:
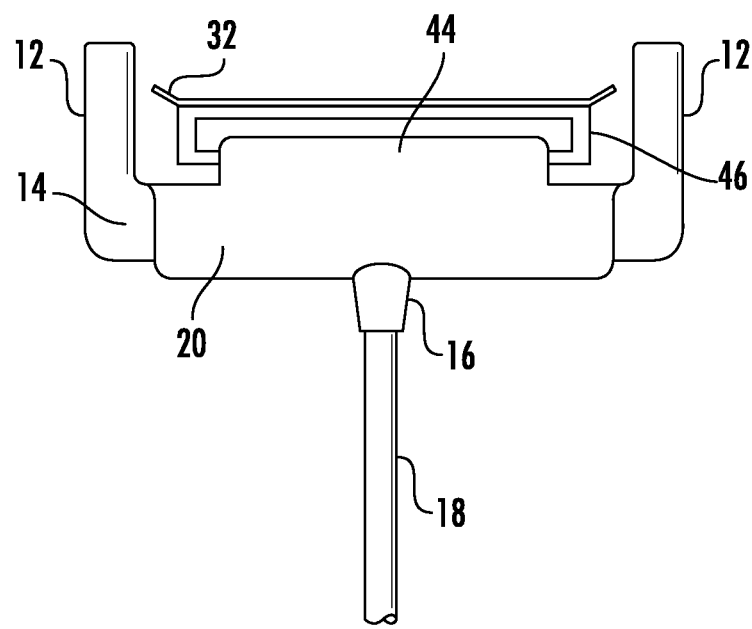
FIG. 13A is a front view of a non-looping nasal cannula device, according to another embodiments of the present invention.
Figure 13B:
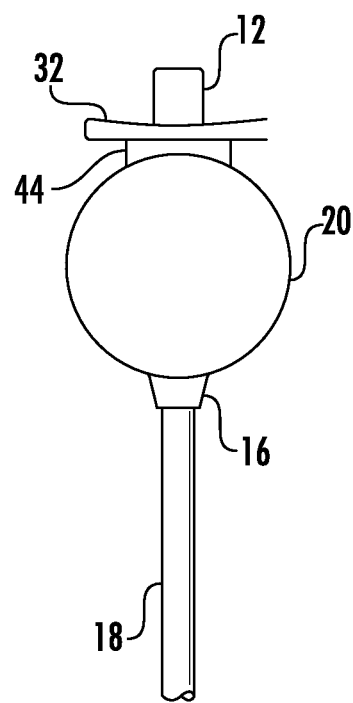
FIG. 13B is a side view of the non-looping nasal cannula device of FIG. 13A.

The attachment device 26 can be releasably or permanently attached to the enclosure 20. In the releasable attachment, the attachment device 26 can be easily removed and/or reattached to the enclosure 20. As an example, the attachment device 26 can be connected to the enclosure 20 via a ball and socket engagement (FIG. 10), a hinge engagement (FIG. 11), a magnet engagement (FIGS. 12A and 12B), a slide engagement (FIGS. 13A and 13B), a hook-and-loop type engagement (e.g., Velcro engagement), and other suitable permanent and releasable connection methods. As an example, FIGS. 12A and 12B show a connection of the attachment device 26 and the enclosure 20 using suitably oriented magnets. The attractive force between opposite poles of two magnets 40A and 40B can hold the enclosure 20 and the attachment device 26 together. As another example, FIGS. 13A and 13B show a slide engagement wherein a hook 44 attached to the enclosure 20 can slide into a matching opening 46. The opening 46 is connected to the adhesive strip 32.

Figure 14A:
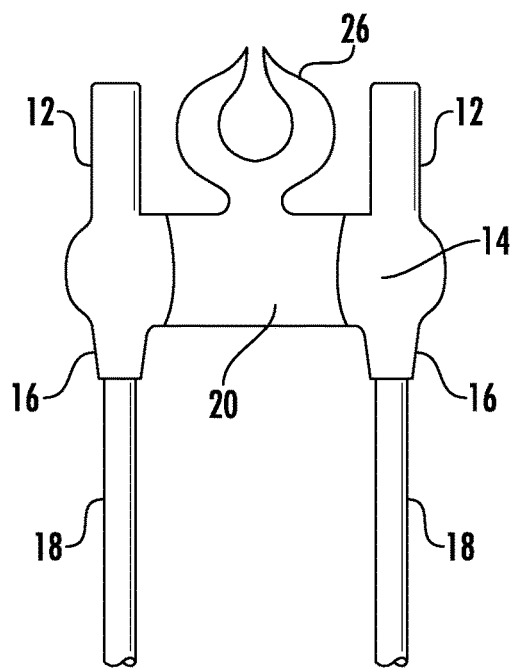
FIG. 14A is a front view of a non-looping nasal cannula device in a retracted position, according to other embodiments of the present invention.
Figure 14B:
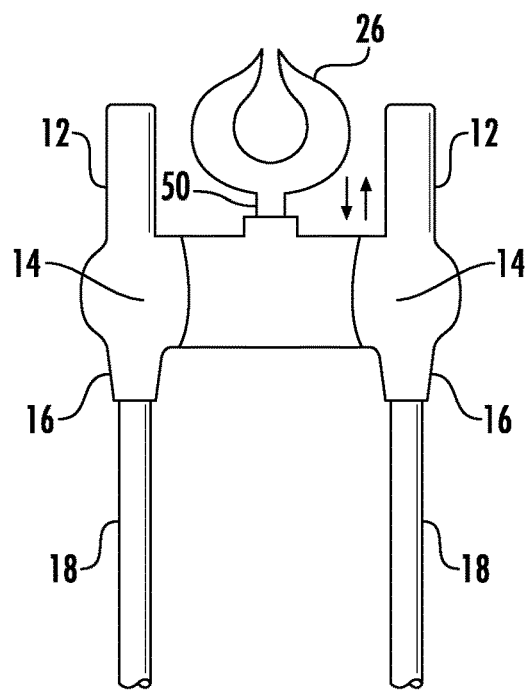
FIG. 14B is a front view of a nasal cannula device of FIG. 14A in extended position.
Figure 15:
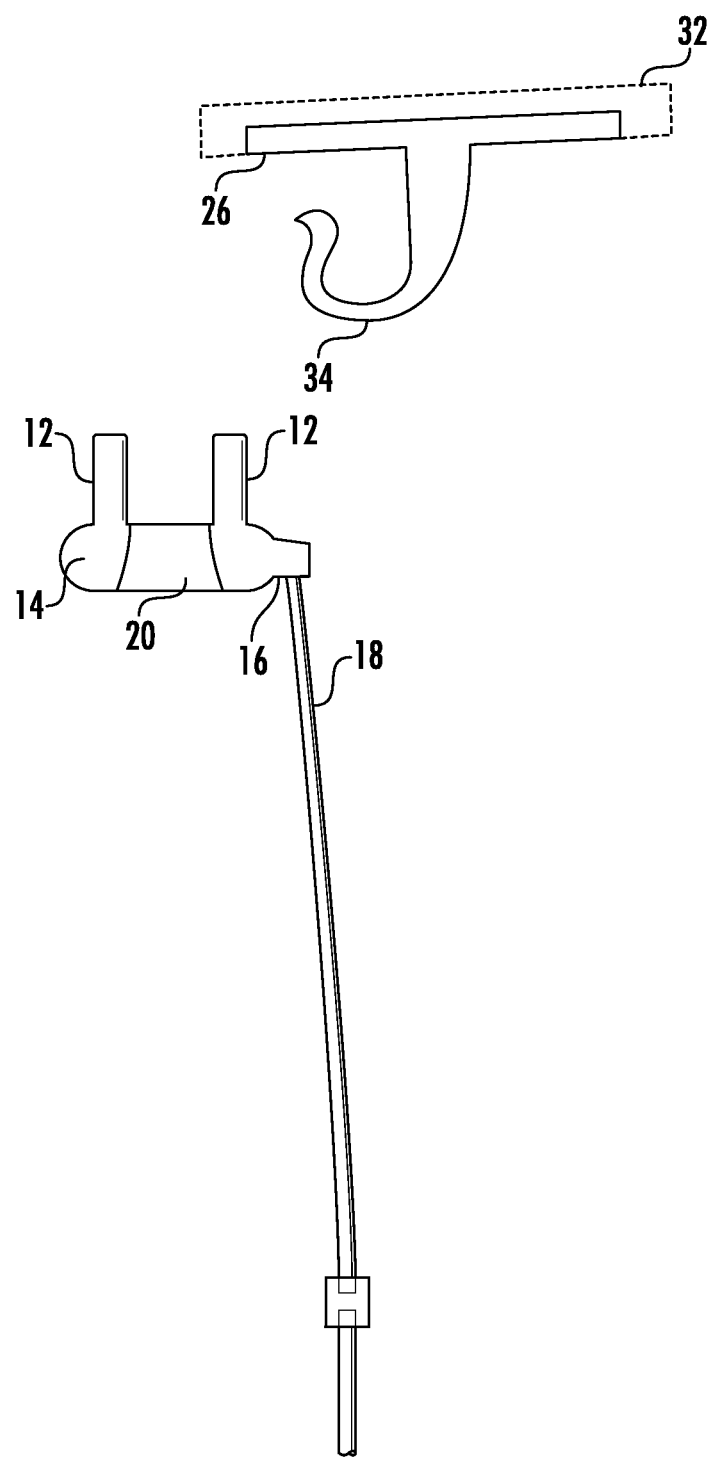
FIG. 15 is a front view of a nasal cannula device of the present invention, according to another embodiment of the present invention.
Figure 16:
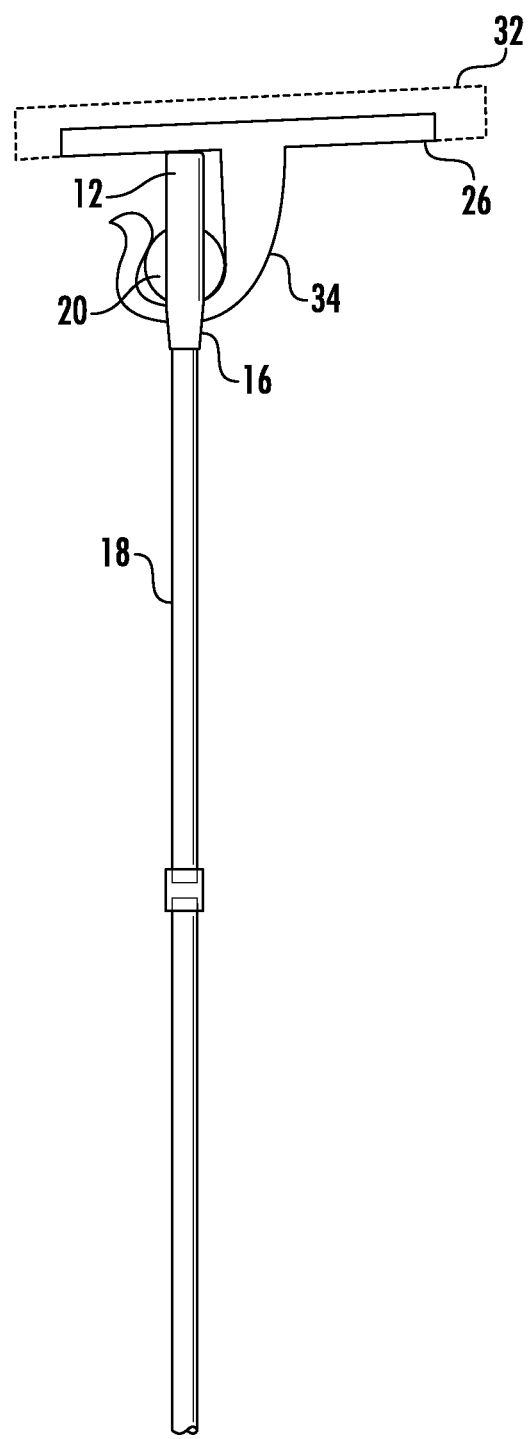
FIG. 16 is a front view of a nasal cannula device of the present invention, according to another embodiment of the present invention.

Referring to FIGS. 14A and 14B, according to another embodiment of the present invention, an extension member 50 can be mounted between the enclosure 20 and the attachment device 26. The extension member 50 can be in a retracted state (FIG. 14A), a partially extended state, or a fully extended state (FIG. 14B) to achieve a desired length for a user. The extension member 50 can introduce a distance between the enclosure 20 and the attachment device 26. For example, the extension member 50 can be designed as a plurality of extendable sections in a telescoping arrangement.

Referring to FIGS. 12A, 13A, 15 and 16, according to another embodiment of the present invention, a pair of legs/prongs can be eliminated altogether. In this case, the attachment device 26 includes an adhesive strip 32 connected to the enclosure 20 via a connection member 34 such as a hook and the like. The adhesive strip 32 is configured to be releasably attached to a user's nose (e.g., columella of the nasal septum, dorsum of the nose, wing of the nose, and/or nostril sill, etc.). The adhesive strip 32 can use medical grade adhesive to hold the strip in place. Example of the medical grade adhesive includes polyurethane-based adhesive. The adhesive can be cured via heat, visible light, UV light and other suitable methods. If needed, additional medical adhesive can be applied to the strip prior to placing it on the columella for extra strength. The strip 32 can be square or any other shape suitable for attaching to the columella. An example dimension of the strip 32 is about 0.64 centimeters in width and about 1.3 centimeters in length. Other dimensions can be used to accommodate a user. The strip 32 can also have a curved base for attachment purpose. The curvature of the base can facilitate placing the strip 32 on the columella more easily and also help to center the strip 32 to the columella. A user can wipe the columella with rubbing alcohol to remove oils before placing the strip 32 on the columella.

Figure 18:
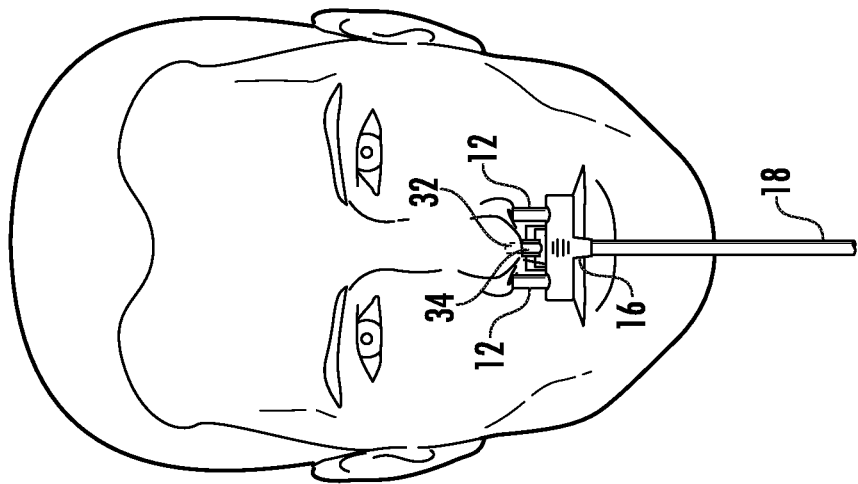
FIG. 18 is a front view of a nasal cannula device of the present invention in use, according to another embodiment of the present invention.
Figure 17:
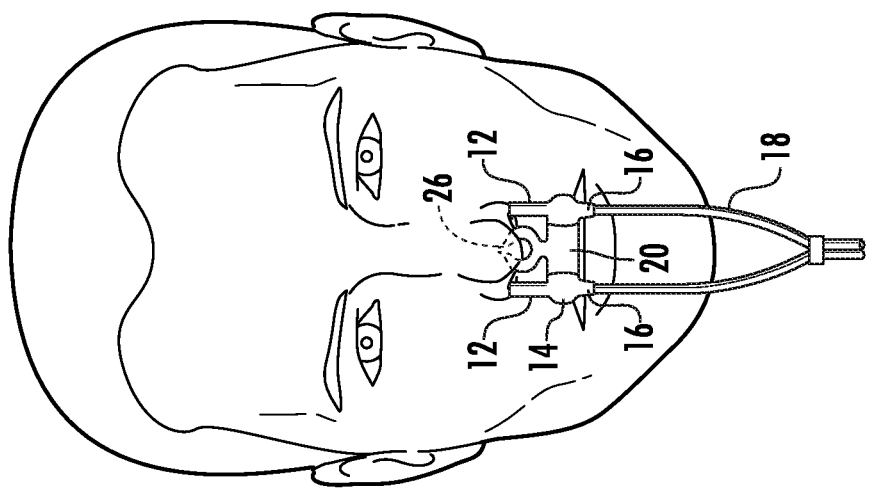
FIG. 17 is front view of a nasal cannula device of the present invention in use, according to another embodiment of the present invention.

According to another embodiment of the present invention, a method of securing an oxygen tube to a patient includes connecting an oxygen tube to the oxygen delivery port and attaching the nasal cannula device to a user's nose or skin in close proximity to a user's nose. In one embodiment, the cannula device includes a pair of opposing legs having a predefined opening therebetween, and the pair of opposing legs slide over a nasal septum and are biased together to provide compression as the pair of legs are moved apart when sliding over the nasal septum, as shown in FIG. 17. In another embodiment, the cannula device can be attached to a user's columella (FIG. 18). The attached cannula device can enable the nasal cannula prongs to slide into the nostrils of the patient to supply oxygen. Oxygen travels through an oxygen tube 18 connected to the oxygen delivery port and is inhaled by the patient through the nose.

The attachment device 26 of the cannula device can be secured to a user before or after connecting an oxygen tube to oxygen delivery port 16. The oxygen tube could, if desired, be removed from the oxygen delivery port 16 prior to or after removal of the attachment device from the user.

The non-looping nasal cannula device can be attached to a user via an attachment device and eliminate the need to loop the oxygen tubes behind the ears. The non-looping nasal cannula reduces the frequency of cannula loss/displacement, decreases the need for replacement of same by nursing staff, and increases patient comfort. It can also significantly improve the quality of life of a patient.

Many additional modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within.

The foregoing is provided for illustrative and exemplary purposes; the present invention is not necessarily limited thereto. Rather, those skilled in the art will appreciate that various modifications, as well as adaptations to particular circumstances, are possible within the scope of the invention as herein shown and described.

What is claimed is:

1. A non-looping nasal cannula device comprising:
   dual nasal prongs extending from a connection bracket and adapted to slide into both nostrils of a user to supply oxygen;
   at least one oxygen delivery port extending from the connection bracket, wherein the at least one oxygen delivery port is configured to be attached to an oxygen tube;
   an attachment device connected to the connection bracket and configured to be attached to at least one of a user's nose or close proximity of the user's nose without looping the oxygen tube behind the user's ears; and
   an enclosure for surrounding the connection bracket, the attachment device being connected to the enclosure;
   wherein the attachment device is connected to the enclosure via at least one of a magnet engagement, a ball and socket engagement, and a hinge engagement.

2. The nasal cannula device of claim 1, wherein the oxygen delivery port extends from a middle portion of the connection bracket.

3. The nasal cannula device of claim 1, wherein the oxygen delivery port extends from at least one end of the connection bracket.

4. The nasal cannula device of claim 1, wherein the attachment device is releasably connected to the connection bracket.

5. The nasal cannula device of claim 1, wherein the attachment device is releasably attached to the enclosure.

6. The nasal cannula device of claim 1, further comprising an extension member mounted between the attachment device and the enclosure for adjusting the distance therebetween.

7. The nasal cannula device of claim 1, wherein the attachment device includes a pair of opposing legs configured to slide over a nasal septum and are biased together to provide compression as the pair of legs are moved apart when sliding over the nasal septum.

8. The nasal cannula device of claim 7, further comprising respective cushions secured to an inside portion of the pair of opposing legs.

9. The nasal cannula device of claim 7, wherein the pair of opposing legs are flexible and the distance between the opposing legs are adjustable, and a pair of gel pads are attached at the end of opposing legs and configured to be attached to an inner surface of user's nostrils.

10. The device of claim 7, wherein the pair of opposing legs are at a distal portion of a prong, and the pair of opposing legs are configured to be manipulated between a closed state and an open state via a proximate end of the prong.

11. A non-looping nasal cannula device comprising:
dual nasal prongs extending from a connection bracket and adapted to slide into both nostrils of a user to supply oxygen;
at least one oxygen delivery port extending from the connection bracket, wherein the at least one oxygen delivery port is configured to be attached to an oxygen tube;
an attachment device connected to the connection bracket and configured to be attached to at least one of a user's nose or close proximity of the user's nose without looping the oxygen tube behind the user's ears;
an enclosure for surrounding the connection bracket, the attachment device being connected to the enclosure; and
an extension member mounted between the attachment device and the enclosure for adjusting the distance therebetween.

12. A method of using a nasal cannula device, the nasal cannula device includes dual nasal prongs extending from a connection bracket and an oxygen delivery port extending from the connection bracket, and the nasal cannula device also includes an attachment device connected to the connection bracket and configured to be attached to a user's nose or close proximity of the user's nose, the method comprising:
connecting an oxygen tube to the oxygen delivery port; and
securing the attachment device to a user's nose or close proximity of the user's nose without looping behind the user's ears;
wherein the nasal cannula device further includes an enclosure surrounding the connection bracket, and the attachment device is connected to the enclosure; and
wherein the nasal cannula device further includes an extension member positioned between the attachment device and the enclosure for adjusting a distance therebetween, the method further comprising adjusting a length of the extension member as desired.

13. The method of claim 12, wherein the attachment device is releasably attached to the enclosure, and the method comprises removing the nasal cannula device from the user via detaching the attachment device from the enclosure.

14. The method of claim 13, wherein the attachment device includes a pair of opposing legs, and the method comprises sliding the pair of opposing legs over a nasal septum to provide compression thereon.

\* \* \* \* \*